(12) United States Patent
Tao

(10) Patent No.: US 8,895,728 B2
(45) Date of Patent: Nov. 25, 2014

(54) METHOD FOR PREPARING CEFMENOXIME HYDROCHLORIDE COMPOUND

(75) Inventor: Linggang Tao, Wuyi (CN)

(73) Assignee: Hainan Lingkang Pharmaceutical Co., Ltd., Hainan (CN)

( * ) Notice: Subject to any disclaimer, the term of this patent is extended or adjusted under 35 U.S.C. 154(b) by 0 days.

(21) Appl. No.: 14/008,542

(22) PCT Filed: Aug. 11, 2011

(86) PCT No.: PCT/CN2011/001331
§ 371 (c)(1),
(2), (4) Date: Sep. 28, 2013

(87) PCT Pub. No.: WO2013/010296
PCT Pub. Date: Jan. 24, 2013

(65) Prior Publication Data
US 2014/0121370 A1     May 1, 2014

(30) Foreign Application Priority Data
Jul. 15, 2011    (CN) .......................... 2011 1 0197613

(51) Int. Cl.
*C07D 513/00*   (2006.01)
*C07D 501/57*   (2006.01)
*C07D 501/00*   (2006.01)

(52) U.S. Cl.
CPC ............ *C07D 501/57* (2013.01); *C07D 501/00* (2013.01)
USPC .......................................................... 544/47

(58) Field of Classification Search
USPC ............................................................ 544/47
See application file for complete search history.

(56) References Cited

FOREIGN PATENT DOCUMENTS

| CN | 101569628 | 11/2009 |
|---|---|---|
| CN | 101798314 | 8/2010 |

OTHER PUBLICATIONS

Donghai Wang et al. Improvement of synthesis process of cefmenoxime hycrochloride. Shandong Chemical Industry. Oct. 1, 2007. 36(12) 1-9.

*Primary Examiner* — T. Victor Oh
(74) *Attorney, Agent, or Firm* — CBM Patent Consulting, LLC

(57) ABSTRACT

A novel process for purifying Cefmenoxime hydrochloride comprises: 1) adding a solvent wherein Cefmenoxime hydrochloride is insoluble at the temperature less than 30° C., filtering after vigorous stirring, washing the filter cake with a solvent wherein Cefmenoxime hydrochloride is insoluble at a temperature less 20° C., and drying; 2) placing the filter cake into ammonium hydroxide, controlling the pH value less than 9 with a gentle agitation to obtain Cefmenoxime acid solution in ammonium hydroxide, and then filtering out the precipitate; 3) adding hydrochloric acid at a concentration of 0.5-4 mol/L to Cefmenoxime acid solution in ammonium hydroxide slowly and controlling the temperature between 30-60° C. and the final pH between 0.5-3.0, and then cooling down to a minimum of 10° C. and standing still to allow crystallization, filtrating and vacuum drying.

16 Claims, No Drawings

METHOD FOR PREPARING CEFMENOXIME HYDROCHLORIDE COMPOUND

FIELD OF THE INVENTION

The present invention relates to a novel process for purifying Cefmenoxime hydrochloride, which belongs to the field of medical technology.

BACKGROUND OF THE INVENTION

Cefmenoxime hydrochloride has a chemical name of (6R, 7R)-7-[(Z)-2-(2-amino-thiazol-4-yl)-2-methoxyiminoacetylamino]-3-[[(1-methyl-1H-tetrazol-5-yl)-sulfanyl]methyl]-8-oxo-5-thia-1-azabicyclo[4.2.0]oct-2-ene-2-carboxylic acid hydrochloride (2:1) with many synonyms such as Bestcall, Azole cephalosporin cefotaxime, Cefmenoxime, Azole hydrochloride cephalosporin cefotaxime, and Cefotaxime azole. It has a chemical formula of $(C_{16}H_{17}N_9O_5S_3)_2 \cdot HCl$ with a molecular weight of 1059.58. The structural formula is

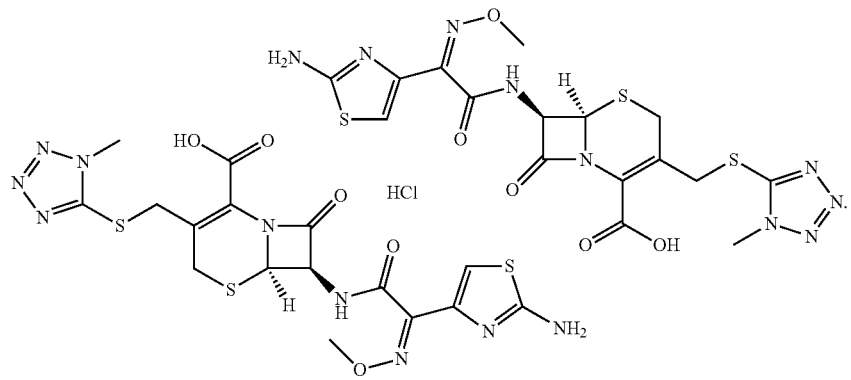 [SMILES: CO/N=C(\C(=O)N[C@@H]1C(=O)N2C(C(=O)O)=C(CSc3nnnn3C)CS[C@H]12)c1csc(N)n1 ; CO/N=C(\C(=O)N[C@@H]1C(=O)N2C(C(=O)O)=C(CSc3nnnn3C)CS[C@H]12)c1csc(N)n1 ; Cl]

Cephalosporins, a β-lactam antibiotic, are a fastest growing antibiotic in the world in recent years with many new varieties. They are an efficient antibiotic with low toxicities. Cefmenoxime hydrochloride is the third-generation semi-synthetic broad-spectrum cephalosporin antibiotic, which was first developed by Takeda Pharmaceutical Co., Ltd. and has been marketed in Japan since 1983. It has entered the latest version of the Pharmacopoeia of Europe and many other countries, and has been marketed in China since 2000.

The key characteristic of the chemical structure of Cefmenoxime hydrochloride is that the acylation of C7-amino side chain and the introduction of methoxy at the 7a position to impart Cefmenoxime hydrochloride a broad-spectrum antibacterial activity. It inhibits cell wall biosynthesis to achieve a bactericidal effect, and has the stability against β-lactamase, and can be used to treat a variety of bacterial infections caused by inflammation with a significant effect (see: Liu Shu Jing, Chen Yaozu. The Research Progress in C3-position Functionalization of Cephalosporins and Synthetic Intermediates thereof [J]. *World Notes on Antibiotics*. 1999, 20 (6): pages 241ff; and Nishimura T, Tabuki K, Hiromatsu K et al, Laboratory and clinical studies of cefmenoxime in the pediatric field [J]. *Jpn J Antibiot*, 1982, 35 (11): 2535-2544).

At present, there are two synthetic routes for producing Cefmenoxime hydrochloride in China: (i) the modification of the side chain at C3 position of 7-ACA and then the amino side chain at C7 position: and (ii) the modification of the amino side chain at C7 position of 7-ACA and then the side chain at C3 position. In these two synthetic routes, Cefmenoxime is prepared and isolated, and then vacuum dried to obtain dry Cefmenoxime acid which is re-dissolved, and then forms salt, and finally yields the finished Cefmenoxime hydrochloride.

Zheng Yimei reported a one-pot Cefmenoxime hydrochloride synthesis technology in the *Chinese Journal of Antibiotics* 33 (5) May (2008). It starts with 3-(1-methyl-1H-tetrazol-5-yl)methyl-7-aminocephalosporanic acid hydrochloride (i.e., 7-ATCA.HCl) available from many manufacturers in China which, as the intermediate, undergoes the condensation reaction with 2-(2-amino-thiazol-4-yl)-2-methoxy imine-acetyl-benzothiazolyl thioester (i.e., AE active ester) to yield Cefmenoxime acid and then forms salt without separation in the reaction solution in a one-pot manner, resulting in Cefmenoxime hydrochloride. Although the process is simplified, the reaction intermediates and reagents tend to be incorporated into the final product.

Pharmaceutical Co. Ltd. Hainan Tianhuang disclosed a method for producing Cefmenoxime hydrochloride in CN101555251A, wherein 7-ATCA, as the starting materials, undergoes a condensation reaction with active ester (AE) to form sodium 7-[α-(2-amino-thiazol-4-yl)-Z-2-methoxyimino acetamido]-3-(1-methyl-1H-5-tetrazolyl-thiomethyl)-3-cephem-4-carboxylate (i.e., sodium Cefmenoxime), and then reacts with 10% hydrochloric acid to yield Cefmenoxime hydrochloride. However, the yield and purity of Cefmenoxime hydrochloride prepared by this method is not high, and moreover triethylamine and ethylene dichloride are used during the preparation the residue of which has a negative impact on the human body.

Chinese patent CN101348494 has disclosed a purification method for refining Cefmenoxime hydrochloride, wherein a macroporous resin is used for adsorption and separation prior to purification by gel column. However, since the adsorption and elution is incomplete, the yield and purity is not ideal, and it is difficult to separate the inherent impurities in Active Pharmaceutical Ingredients.

At present, most Chinese manufacturers of Cefmenoxime hydrochloride formulations rely on imports of Active Pharmaceutical Ingredients for packing drugs, although a few Chinese manufacturers produce the product by themselves, but the yield and purity of the product is not very high. Therefore, improving the purity of Cefmenoxime hydrochloride is an urgent problem with significant social and economic benefits.

SUMMARY OF THE INVENTION

To overcome the above deficiencies of the prior art, especially the deficiency of the low purity of Cefmenoxime hydrochloride prepared in the prior art, the present invention provides a novel method for refining Cefmenoxime hydrochloride.

Cefmenoxime hydrochloride to be refined according to the method of the present invention is crude Cefmenoxime hydrochloride obtained by currently known synthetic methods, or commercially available or imported Active Pharmaceutical ingredients of Cefmenoxime hydrochloride, which are collectively referred to as raw Cefmenoxime hydrochloride in the present invention.

After a delicate study, the inventor has found that the purity of raw Cefmenoxime hydrochloride, can be significantly improved by a purification method comprising the following processing steps:

step 1) adding a solvent wherein Cefmenoxime hydrochloride is insoluble to the raw Cefmenoxime hydrochloride while controlling the temperature no higher than 30° C., filtering after vigorous stirring, washing the filter cake with a solvent wherein Cefmenoxime hydrochloride is insoluble at a temperature no higher than 20° C., and drying in vacuum or in the air;

step 2) placing the filter cake into ammonium hydroxide (namely aqueous ammonia), controlling the pH value no more than 9 with a gentle agitation to obtain Cefmenoxime acid solution in ammonium hydroxide, and then filtering out the precipitate; and step 3) adding hydrochloric acid at a concentration of 0.5-4 mol/L to the Cefmenoxime acid solution in ammonium hydroxide slowly and controlling and maintaining the temperature between 30 and 60° C. and the final pH between 0.5 and 3.0 for 30 minutes to 5 hours, and then cooling gradually down to a minimum of 10° C. and standing still to allow crystallization, filtrating and vacuum drying to obtain the refined Cefmenoxime hydrochloride.

DESCRIPTION OF THE PREFERRED EMBODIMENTS

The steps of the method for purifying Cefmenoxime hydrochloride according to the present invention is detailed hereafter.

step 1) adding a solvent wherein Cefmenoxime hydrochloride is insoluble to the raw Cefmenoxime hydrochloride while controlling the temperature no higher than 30° C., filtering after vigorous stirring, washing the filter cake with a solvent wherein Cefmenoxime hydrochloride is insoluble at a temperature no higher than 20° C., and drying in vacuum or in the air.

Generally, the raw Cefmenoxime hydrochloride to be purified according to the present invention may contain organic solvents, a variety of raw materials and intermediate products introduced during the preparation, such as solvents for example dichloromethane used in the prior art, the starting materials for example 7-ATCA.HCl or 7-ATCA and AE active ester, Cefmenoxime acid or sodium Cefmenoxime formed during the preparation, as well as polymers generated during post-processing or storage which are more easily generated during handling or storing at higher temperatures.

The inventors have noted that these impurities mainly lead to no high purity of raw Cefmenoxime hydrochloride. They not only reduce the content of active pharmaceutical ingredients, but also deepen the color of the resulting product. Due to failure to take specific purification of these impurities, they generally remain mixed with raw Cefmenoxime hydrochloride.

The inventors found that these organic impurities have a great solubility in organic solvents, whereas Cefmenoxime hydrochloride is almost insoluble in ethanol, acetone or ethyl acetate. According to the instant invention, after the treatment of step 1), these impurities can be separated from Cefmenoxime hydrochloride.

According to a preferred embodiment of the present invention, a solvent wherein Cefmenoxime hydrochloride is insoluble is added into the raw Cefmenoxime hydrochloride, preferably ethanol, acetone or ethyl acetate, more preferably ethanol or ethyl, most preferably ethyl acetate. With vigorous stirring, the temperature is controlled no higher than 30° C., preferably no higher than 25° C., more preferably no higher than 20° C.

We found that if the temperature at which a solvent wherein Cefmenoxime hydrochloride is insoluble is added is too higher, the loss of the target compound is likely to be caused due to dissolution. If the temperature is even higher, such as higher than 80° C., degradation and polymerization of Cefmenoxime hydrochloride will lead to a reduction in the content of active pharmaceutical ingredients, deepening of the color, and an increase in the content of polymer impurities. The lower the temperature, the less soluble Cefmenoxime hydrochloride in organic solvents, but the too low temperature also affects removal of organic impurities to be dissolved.

After the above treatment, the impurities dissolved in the solvent is filtered, and the filter cake is washed with a solvent wherein Cefmenoxime hydrochloride is insoluble, such as ethanol, acetone or ethyl acetate, at a temperature no higher than 20° C., preferably no higher than 15° C. more preferably no higher than 12° C.

In a preferred embodiment of the present invention, the washing solvent is preferably the same as the solvent for dissolving the raw Cefmenoxime hydrochloride During the drying process, in order to prevent Cefmenoxime hydrochloride from decomposition, the drying is done preferably by air-drying or vacuum drying at room temperature.

Step 2), the filter cake is placed into ammonium hydroxide (namely aqueous ammonia), controlling the pH value no more than 9 with a gentle agitation to obtain Cefmenoxime acid solution in ammonium hydroxide, and then the insoluble precipitate in the Cefmenoxime acid solution is filtered out.

Without being bound to any theory, the ammonium hydroxide treatment is employed in the inventive step 2) for the following reasons:

Cefmenoxime exists in the form of either Cefmenoxime acid or Cefmenoxime hydrochloride, depending on the pH control. At a higher pH, it exists in the form of Cefmenoxime hydrochloride; at a lower pH, it exists in the form of Cefmenoxime acid.

In addition to Cefmenoxime hydrochloride, the filter cake obtained from the step 1) contains a trace of catalyst, salts and heavy metals and other inorganic substances introduced during the preparation, as well as bacterial endotoxins generated during the storage. These substances are generally difficult to dissolve in organic solvents, and thus not removed in the step 1). With the gradual increase of pH due to the ammonium hydroxide added, Cefmenoxime hydrochloride is converted into Cefmenoxime acid and dissolves in aqueous alkaline solution, whereas some inorganic substances are able to form basic salt precipitation and be removed by filtration, thereby effectively reducing the impurities.

According to a preferred embodiment of the present invention, the concentration of the ammonium hydroxide added to the filter cake from the step 1) is 15-25%, and the filter cake is treated with the ammonium hydroxide for preferably from 30 minutes to 6 hours, more preferably 1-5 hours, most preferably 2-3 hours, until the aqueous solution becomes weak alkaline with a pH value of preferably not more than 9, more preferably not more than 8.5, most preferably not more than 8. In this treating process, it is under stirring so as to achieve a full mix, and then the precipitation is filtered out.

According to a preferred embodiment of the present invention, the aqueous solution after filtration is heated to 30-60° C., preferably 35-55° C. more preferably 40-50° C., on one hand to remove the remaining ammonia in aqueous solution, and on the other hand to facilitate the subsequent crystallization step.

Step 3) Hydrochloric acid is added slowly at a concentration of 0.5-4 mol/L to the Cefmenoxime acid solution in ammonium hydroxide, controlling and maintaining the temperature between 30 and 60° C. and the final pH between 0.5 and 3.0 for 30 minutes to 5 hours, and then the temperature is cooled gradually down to a minimum of 10° C. The solution stands still to allow crystallization, and the refined Cefmenoxime hydrochloride is obtained after filtrating and vacuum drying.

It is found in our study that at a lower acidity value, i.e. a higher pH of the alkaline condition. Cefmenoxime exists in a form of Cefmenoxime acid or in a basic salt form of Cefmenoxime acid, and at this time, without separation and drying, simply increasing the acidity value, that is, adjusting the pH value into acidic will lead to Cefmenoxime hydrochloride.

Although Cefmenoxime hydrochloride is soluble in formamide and slightly soluble in methanol, it is difficult to achieve good crystallization by dissolving in these solvents or suspending in other solvents commonly used and then refluxing with stirring. Treating Cefmenoxime hydrochloride crude directly with a good-poor solvent precipitation method can not achieve the desired purity.

Surprisingly, it is found that, after the inventive treatment of the above steps 1) and 2), through a rational choice of the concentration of hydrochloric acid and controlling an appropriate pH, Cefmenoxime hydrochloride can crystallize from water to obtain high purity crystals. The reason may be that the impurities having an adverse effect on the crystallization have been removed through the inventive steps 1) and 2), improving the purity of the mother liquor for crystallization, and moreover Cefmenoxime hydrochloride formed after adding hydrochloric acid into the ammonium hydroxide-treated Cefmenoxime is more suitable for the direct crystallization from water.

According to a preferred embodiment of the present invention, the concentration of the hydrochloric acid added slowly to the Cefmenoxime acid solution in ammonium hydroxide is 0.5-4 mol/L, preferably 0.8-3 mol/L, more preferably 1.0-2 mol/L, with the temperature controlled at 30-60° C., preferably 40-55° C. more preferably 45-50° C., and with the final pH controlled within 0.5-3.0, preferably 0.8-2.5, more preferably 1.0-2.0, for 30 minutes to 5 hours, preferably for 50 minutes to 3 hours, more preferably for 1-2 hours. Within this time period, crystals precipitate from the solution slowly.

Then, the temperature is gradually cooled down to a minimum of 10° C., preferably a minimum of 12° C., more preferably a minimum of 15° C., and the solution stands still to allow crystallization, and thus the refined Cefmenoxime hydrochloride is obtained through filtrating and vacuum drying.

Generally, the more the temperature drops, the more Cefmenoxime hydrochloride precipitates, but the inventors found that below 10° C., Cefmenoxime hydrochloride tends to precipitate in a form of powder rather than crystals and carry more solvents or impurities.

Cefmenoxime hydrochloride seeds are optionally added in the cooling process. Oversaturation could easily happen in the cooling process, especially when it is about to start crystallization, but adding the seeds can effectively prevent from forming excessive small nuclei, inhibit primary nucleation, and reduce coalescence, facilitating the crystal growth.

According to a preferred embodiment of the present invention, adding an organic solvent in the crystallization process such as alcohols for example methanol, ethanol, isopropyl alcohol; acetone or ethyl acetate, not only improves the crystallization rate, but also improves the product yield. These solvents can be used alone or in combination. The addition amount of such solvent(s) accounts for 10-20%, preferably 12-18%, most preferably 15% of the volume of the crystallization mother liquor.

The crystallization is complete after standing still for 2-24 hours, and then drying such as air drying or drying in an oven is used.

According to a preferred embodiment of the present invention, concentration of the aqueous Cefmenoxime hydrochloride solution can be done while the aqueous solution is heated to remove the remaining ammonia in the step 2), that is, the final heating of the aqueous solution in the step 2), on one hand removes the remaining ammonia, and on the other hand facilitates concentration of the aqueous Cefmenoxime hydrochloride solution. As a result, the crystallization process of the step 3) can proceed directly without cooling.

Step 4), the mother liquor after crystallization is optionally subjected again to the step 3).

As the crystallization mother liquor is obtained in the step 3) by precipitation after cooling gradually down to a minimum of 10° C. preferably a minimum of 12° C. more preferably a minimum of 15° C., it contains a certain amount of Cefmenoxime hydrochloride which has not precipitated. The crystallization mother liquor is subjected to the step 3) once more to allow crystallization again, improving the yield of Cefmenoxime hydrochloride greatly.

As measured by High Performance Liquid Chromatography (Chinese Pharmacopoeia 2005 Edition, Volume II, Appendix VD), the purity converted into Cefmenoxime hydrochloride of the refined Cefmenoxime hydrochloride obtained according to the above embodiments is not less than 99.2%, and usually not less than 99.4%. And the THF content is lower than 0.03%: the N, N-dimethylacetamide content is lower than 0.05%; the methylene chloride content is less than 0.02%: residue on ignition is less than 0.02%: heavy metals are less than 10 ppm; and the polymer impurity content is less than 0.06%. The insoluble particle content in the obtained injection is very low.

In view of the great impact of the powder flowability, intrinsic dissolution rate, solid stability and preparation operability of Cefmenoxime hydrochloride on the activity exhibited and the preparation formulated, a great improvement in the purity of Cefmenoxime hydrochloride would improve substantially the dissolution rate, the formulatability and the stability.

Therefore, the refined Cefmenoxime hydrochloride according to a purification method of the present invention is well suitable for preparing antimicrobial pharmaceutical compositions comprising the refined Cefmenoxime hydrochloride according to a purification method of the present invention and a pharmaceutically acceptable excipient for treating various inflammations caused by bacterial infections. Preferably, the pharmaceutical composition can be in freeze-dried powder or in an injectable preparation.

The present invention also provides the use of the above pharmaceutical composition in the manufacture of a medicament for the treatment of bacterial infections caused by a variety of inflammation. Preferably, the above infections include pneumonia, bronchitis, biliary tract infections, peritonitis, and urinary tract infections.

The present invention fundamentally changes the low-purity status of raw Cefmenoxime hydrochloride all over the world, addresses the challenge crude Cefmenoxime hydrochloride and Active Pharmaceutical Ingredients of Cefmenoxime hydrochloride facing, improves a series of clinical adverse reactions caused by insoluble particles or polymer impurities, improves the quality of finished products, and reduces toxic side effects. The method of the present invention also has advantages such as simpleness, control easiness, and easiness for industrial production.

The following examples further illustrate the invention. These examples are for the purpose of illustration and are not to be construed as a limitation upon the following appended claims.

I. HPLC Determination of the Cefmenoxime Hydrochloride Purity:

Chromatographic conditions and system suitability test: octadecyl silane bonded silane is the filler; acetonitrile-water-acetic acid (10:50:1) is the mobile phase, detection wavelength is 254 nm; theoretical plate number calculated by the Cefmenoxime hydrochloride peak should not be less than 1000; and peak separation of Cefmenoxime hydrochloride peak and adjacent impurity peaks should meet the requirements.

Determination: accurately weigh out an appropriate amount of Cefmenoxime hydrochloride sample, dissolve in an appropriate amount of a phosphate buffer (pH 6.8), and then formulate a solution containing 0.1 mg per 1 ml with mobile phase. Inject 20 µL into the liquid chromatograph and record the chromatogram, and at the same time an appropriate amount of the Cefmenoxime hydrochloride standard is measured as control with the same method. The Cefmenoxime content in the sample is calculated with an external standard method on the basis of the peak area, and then converted into the Cefmenoxime hydrochloride purity.

II. Determination of Polymer Content:

Sephadex G-10 gel chromatography system is used to check and measure the polymer impurities in Cefmenoxime hydrochloride.

III. Determination of Related Substances:

Related substances are determined according to the method described in Standard YBH09262006 issued by Chinese National Food and Drug Administration.

Example 1

100 g of crude Cefmenoxime hydrochloride obtained according to CN101555251A was weighed out. The Cefmenoxime hydrochloride content was 89% as measured by high performance liquid chromatography. The polymer content was 4% as measured by gel permeation chromatography system. Ethanol was added to the crude Cefmenoxime hydrochloride with the temperature controlled no higher than 28° C. After vigorous agitation, the solution was filtered. The filter cake was washed with ethanol at a temperature no higher than 20° C. and then air dried.

The filter cake was placed into ammonium hydroxide with a concentration of 20%. The filter cake was treated with the ammonium hydroxide under stirring for 2 hours until the aqueous solution becomes weak alkaline with a pH value of preferably not more than 8.5. Then the precipitate was filtered out. The aqueous solution after filtration is heated to 40° C. to remove the remaining ammonia in the aqueous solution.

Hydrochloric acid at a concentration of 2 mol/L was added to the obtained Cefmenoxime acid solution in ammonium hydroxide slowly with the temperature controlled at 40° C. and the final pH at 2.0. The solution was maintained for 1 hour, and crystals precipitated slowly. Then the temperature was cooled gradually down to a minimum of 12° C. The solution was allowed to stand still for crystallization, and a white Cefmenoxime hydrochloride 88 g was obtained after filtration and vacuum drying.

| | $^1$H NMR data: | | | | |
|---|---|---|---|---|---|
| Proton # | Chemical Shift (ppm) 400 MHz | | Multiplicity and Proton Numbers | Assignment of Protons | Note |
| | Sample | literature* | | | |
| a | 3.70 | 3.67 | 2H q. | As shown in the following structure | |
| b | 3.89 | 3.89 | 3H s. | | |
| c | 3.94 | 3.91 | 3H s. | | |
| d | 4.29 | 4.27 | 2H q. | | |
| e | 5.14 | 5.09 | 1H d. | | |
| f | 5.77 | 5.71 | 1H dd. | | |
| g | 6.83 | 6.80 | 1H s. | | |
| h | 8.01 | — | 2H | | Disappearance upon exchange with $D_2O$ |
| i | 9.71 | 9.65 | 1H d. | | Incomplete disappearance upon exchange with $D_2O$ |
| j | 13.60 | — | 1H | | Disappearance upon exchange with $D_2O$ |

*J. Antibio 1981, 34 (2): 171

The corresponding structure is shown as follows.

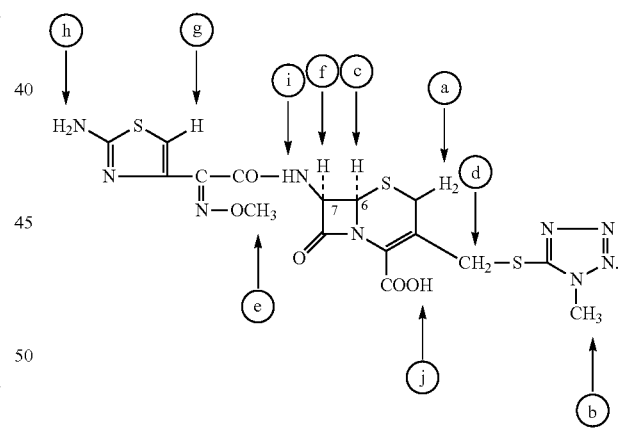

The Cefmenoxime purity as measured by high-performance liquid chromatography is 99.2%. The polymer impurity content is 0.06% as determined by gel chromatography. The tetrahydrofuran content is 0.03%. The N,N-dimethylacetamide content is 0.05%. The methylene chloride content is 0.02%. Residue on ignition is 0.02%. No heavy metals were detected. The refined product is formulated with water into a clear and colorless solution containing about 0.1 g per 1 ml.

Comparative Example 1

The crude Cefmenoxime hydrochloride used in Example 1 was purified according to the purification method described in China's patent. CN101348494. The Cefmenoxime purity measured by high performance liquid chromatography was 92%. The polymer impurity content as measured by gel chromatography was 2%.

Example 2

100 g Cefmenoxime hydrochloride API (Zhejiang Jianfeng Pharmaceutical Ltd., batch number 20110203) was weighed out. The Cefmenoxime purity as measured by high performance liquid chromatography was 91%. The polymer impurity content as measured by gel chromatography was 1.5%. Ethyl acetate was added to the crude Cefmenoxime hydrochloride with the temperature controlled no higher than 25° C. After vigorous agitation, the solution was filtered. The filter cake was washed with ethyl acetate at a temperature no higher than 16° C. and then vacuum dried.

The filter cake was placed into ammonium hydroxide with a concentration of 23%. The filter cake was treated with the ammonium hydroxide under stirring for 3 hours until the aqueous solution becomes weak alkaline with a pH value of preferably not more than 9. Then the precipitate was filtered out. The aqueous solution after filtration is heated to 45° C. to remove the remaining ammonia in the aqueous solution.

Hydrochloric acid at a concentration of 3 mol/L was added to the obtained Cefmenoxime acid solution in ammonium hydroxide slowly with the temperature controlled at 50° C. and the final pH at 2.5. The solution was maintained for 2 hours, and during this process ethanol was added at an amount which accounts for about 15% of the volume of the crystallization mother liquor. During the slow cooling, Cefmenoxime hydrochloride seeds were added, and crystals precipitated slowly. Then the temperature was cooled gradually down to a minimum of 15° C. The solution was allowed to stand still for crystallization, and a white Cefmenoxime hydrochloride 90 g was obtained after filtration and vacuum drying.

The Cefmenoxime purity as measured by high-performance liquid chromatography is 99.4%. The polymer impurity content is 0.05% as determined by gel chromatography. The tetrahydrofuran content is 0.02%. The N,N-dimethylacetamide content is 0.04%. The methylene chloride content is 0.02%. Residue on ignition is 0.02%. No heavy metals were detected. The refined product is formulated with water into a clear and colorless solution containing about 0.1 g per 1 ml.

Example 3

100 g Cefmenoxime hydrochloride API which had been stored for a longer time (Zhejiang Jianfeng Pharmaceutical Ltd. batch number 20080701) was weighed out. The Cefmenoxime purity as measured by high performance liquid chromatography was 85%. The polymer impurity content as measured by gel chromatography was 9%. Ethyl acetate was added to the crude Cefmenoxime hydrochloride with the temperature controlled no higher than 25° C. After vigorous agitation, the solution was filtered. The filter cake was washed with ethyl acetate at a temperature no higher than 15° C., and then vacuum dried.

The filter cake was placed into ammonium hydroxide with a concentration of 20%. The filter cake was treated with the ammonium hydroxide under stirring for 4 hours until the aqueous solution becomes weak alkaline with a pH value of preferably not more than 8. Then the precipitate was filtered out. The aqueous solution after filtration is heated to 50° C. to remove the remaining ammonia in the aqueous solution.

Hydrochloric acid at a concentration of 4 mol/L was added to the obtained Cefmenoxime acid solution in ammonium hydroxide slowly with the temperature controlled at 45° C. and the final pH at 1.5. The solution was maintained for 2 hours, and during this process ethanol was added at an amount which accounts for about 10% of the volume of the crystallization mother liquor. During the slow cooling, Cefmenoxime hydrochloride seeds were added, and crystals precipitated slowly. Then the temperature was cooled gradually down to a minimum of 12° C. The solution was allowed to stand still for crystallization, and a white Cefmenoxime hydrochloride 84 g was obtained after filtration and vacuum drying.

The Cefmenoxime purity as measured by high-performance liquid chromatography is 99.3%. The polymer impurity content is 0.06% as determined by gel chromatography. The tetrahydrofuran content is 0.02%. The N,N-dimethylacetamide content is 0.04%. The methylene chloride content is 0.01%. Residue on ignition is 0.02%. No heavy metals were detected. The refined product is formulated with water into a clear and colorless solution containing about 0.1 g per 1 ml.

Example 4

100 g expired Cefmenoxime hydrochloride API was weighed out. The Cefmenoxime purity as measured by high performance liquid chromatography was 82%. The polymer impurity content as measured by gel chromatography was 10%. Acetone was added to the crude Cefmenoxime hydrochloride with the temperature controlled no higher than 22° C. After vigorous agitation, the solution was filtered. The filter cake was washed with acetone at a temperature no higher than 13° C., and then vacuum dried.

The filter cake was placed into ammonium hydroxide with a concentration of 18%. The filter cake was treated with the ammonium hydroxide under stirring for 2 hours until the aqueous solution becomes weak alkaline with a pH value of preferably not more than 8.5. Then the precipitate was filtered out. The aqueous solution after filtration is heated to 45° C. to remove the remaining ammonia in the aqueous solution.

Hydrochloric acid at a concentration of 3 mol/L was added to the obtained Cefmenoxime acid solution in ammonium hydroxide slowly with the temperature controlled at 40° C. and the final pH at 1.2. The solution was maintained for 3 hours, and during this process ethanol was added at an amount which accounts for about 12% of the volume of the crystallization mother liquor. During the slow cooling, Cefmenoxime hydrochloride seeds were added, and crystals precipitated slowly. Then the temperature was cooled gradually down to a minimum of 14° C. The solution was allowed to stand still for crystallization, and a white Cefmenoxime hydrochloride 81 g was obtained after filtration and vacuum drying.

The Cefmenoxime purity as measured by high-performance liquid chromatography is 99.2%. The polymer impurity content is 0.06% as determined by gel chromatography. The tetrahydrofuran content is 0.03%. The N,N-dimethylacetamide content is 0.04%. The methylene chloride content is 0.02%. Residue on ignition is 0.02%. No heavy metals were detected. The refined product is formulated with water into a clear and colorless solution containing about 0.1 g per 1 ml.

The invention has been described with reference to exemplary embodiments. It should be understood that these exemplary embodiments are only for the purpose of illustration. Without depart of the spirit and essential of the invention, modifications and alterations will occur to the person skilled in the art upon reading and understanding the preceding detailed description. Therefore, such modifications and alterations are intended to be included within the scope of the appended claims.

What is claimed is:

1. A novel process for purifying Cefmenoxime hydrochloride of the following formula, characterized in that the process comprises:

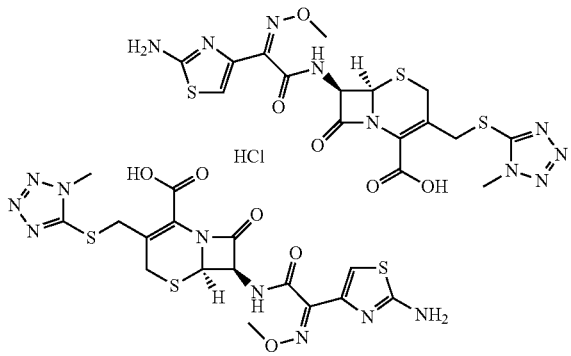 [SMILES: CO/N=C(\C(=O)N[C@@H]1C(=O)N2C(C(=O)O)=C(CSc3nnnn3C)CS[C@H]12)c1csc(N)n1 ; CO/N=C(\C(=O)N[C@@H]1C(=O)N2C(C(=O)O)=C(CSc3nnnn3C)CS[C@H]12)c1csc(N)n1 ; Cl]

step 1) adding a solvent wherein Cefmenoxime hydrochloride is insoluble to the raw Cefmenoxime hydrochloride while controlling the temperature at the range between 10 and 30° C., filtering after vigorous stirring, washing the filter cake with a solvent wherein Cefmenoxime hydrochloride is insoluble at a temperature between 0 and 20° C., and drying in vacuum or in the air;

step 2) placing the filter cake into ammonium hydroxide, controlling the pH value between 7 and 9 with a gentle agitation to obtain Cefmenoxime acid solution in ammonium hydroxide, and then filtering out the precipitate;

step 3) adding hydrochloric acid at a concentration of 0.5-4 mol/L to the Cefmenoxime acid solution in ammonium hydroxide and controlling the temperature between 30° C. and 60° C., and the final pH between 0.5 and 3.0 in 30 minutes to 5 hours, and then cooling down to 10° C. and standing still to allow crystallization, filtrating and vacuum drying to obtain the refined Cefmenoxime hydrochloride; and step 4) optionally, recycling the remaining liquid of step 3) for the recrystallization in step 3).

2. The process according to claim 1, wherein
the solvent in step 1) is one or more reagent selected from the group consisting of ethanol, acetone and ethyl acetate; and the temperature during the vigorous stirring is between 10 and 30° C.

3. The process according to claim 1, wherein the temperature is between 5 to 20° C. when the filter cake is washed in step 1); the washing solvent is the same as the solvent for dissolving the raw Cefmenoxime hydrochloride; and the drying temperature in step 1) is room temperature.

4. The process according to claim 1, wherein the concentration of the ammonium hydroxide in step 2) added to the filter cake from step 1) is between 15 and 25%, and the filter cake is treated with the ammonium hydroxide under stirring for 1 to 5 hours until the aqueous solution has a pH value between 7 and 9.

5. The process according to claim 1, wherein the aqueous solution after filtration in step 2) is heated to the temperature between 35 and 55° C.

6. The process according to claim 1, wherein the concentration of the hydrochloric acid in step 3) is between 0.8 and 3 mol/L while the temperature is between 40 and 55° C. and the final pH is between 0.8 and 2.5, the addition of the hydrochloric acid takes for 50 minutes to 3 hours; and then the temperature is cooled down to a range between 0 and 12° C.

7. The process according to claim 1, wherein an organic solvent in step 3) is one or more reagent selected from the group consisting of methanol, ethanol, isopropyl alcohol, acetone and ethyl acetate, and the amount of the organic solvent used in step 3) is 12-18% of the volume of the crystallization solution.

8. The process according to claim 1, wherein the temperature of the remaining liquid after crystallization in step 4) is between 0 and 12° C.

9. A process for purifying Cefmenoxime hydrochloride comprises:

step 1) adding a solvent wherein Cefmenoxime hydrochloride is insoluble to the raw Cefmenoxime hydrochloride while controlling the temperature at the range between 10 and 30° C., filtering after vigorous stirring, washing the filter cake with a solvent wherein Cefmenoxime hydrochloride is insoluble at a temperature between 0 and 20° C., and drying in vacuum or in the air;

step 2) placing the filter cake into ammonium hydroxide, controlling the pH value between 7 and 9 with a gentle agitation to obtain Cefmenoxime acid solution in ammonium hydroxide, and then filtering out the precipitate;

step 3) adding hydrochloric acid at a concentration of 0.5-4 mol/L to the Cefmenoxime acid solution in ammonium hydroxide slowly and controlling the temperature between 30° C. and 60° C. and the final pH between 0.5 and 3.0 in 30 minutes to 5 hours, adding Cefmenoxime hydrochloride seeds, and then cooling down to 10° C. and standing still to allow crystallization, filtrating and vacuum drying to obtain the refined Cefmenoxime hydrochloride; and step 4) optionally, recycling the remaining liquid of step 3) for the recrystallization in step 3).

10. The process according to claim 9, wherein the solvent in step 1) is one or more reagent selected from the group consisting of ethanol, acetone and ethyl acetate; and the temperature during the vigorous stirring is between 10 and 30° C.

11. The process according to claim 9, wherein the temperature is between 5 to 20° C. when the filter cake is washed in step 1); the washing solvent is the same as the solvent for dissolving the raw Cefmenoxime hydrochloride; and the drying temperature in step 1) is room temperature.

12. The process according to claim 9, wherein the concentration of the ammonium hydroxide in step 2) added to the filter cake from step 1) is between 15 and 25%, and the filter cake is treated with the ammonium hydroxide under stirring for 1 to 5 hours until the aqueous solution has a pH value between 7 and 9.

13. The process according to claim 9, wherein the aqueous solution after filtration in step 2) is heated to the temperature between 35 and 55° C.

14. The process according to claim 9, wherein the concentration of the hydrochloric acid in step 3) is between 0.8 and 3 mol/L while the temperature is between 40 and 55° C. and the final pH is between 0.8 and 2.5, the addition of the hydrochloric acid takes for 50 minutes to 3 hours; and then the temperature is cooled down to a range between 0 and 12° C.

15. The process according to claim 9, wherein an organic solvent in step 3) is one or more reagent selected from the group consisting of methanol, ethanol, isopropyl alcohol, acetone and ethyl acetate, and the amount of the organic solvent used in step 3) is 12-18% of the volume of the crystallization solution.

16. The process according to claim 9, wherein the temperature of the remaining liquid after crystallization in the step 4) is between 0 and 12° C.

\* \* \* \* \*